(12) United States Patent
Aso

(10) Patent No.: US 8,485,023 B2
(45) Date of Patent: Jul. 16, 2013

(54) SOLVENT DELIVERY PUMP AND LIQUID CHROMATOGRAPH

(75) Inventor: Yoshiaki Aso, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 241 days.

(21) Appl. No.: 13/189,985

(22) Filed: Jul. 25, 2011

(65) Prior Publication Data
US 2012/0031174 A1    Feb. 9, 2012

(30) Foreign Application Priority Data
Aug. 3, 2010    (JP) .................................. 2010-174239

(51) Int. Cl.
*G01N 1/00*    (2006.01)
*F04B 41/06*    (2006.01)

(52) U.S. Cl.
USPC .......................................... 73/61.56; 417/521

(58) Field of Classification Search
USPC ................ 73/61.52, 61.55, 61.56; 210/198.2, 210/198.3
See application file for complete search history.

(56) References Cited

U.S. PATENT DOCUMENTS

| | | | | |
|---|---|---|---|---|
| 3,934,456 A | * | 1/1976 | Munk | 73/61.55 |
| 5,938,416 A | * | 8/1999 | Saito et al. | 417/521 |
| 2009/0193879 A1 | * | 8/2009 | Yasuhara et al. | 73/61.56 |

FOREIGN PATENT DOCUMENTS

JP    10-238475 A    9/1998

* cited by examiner

*Primary Examiner* — Hezron E Williams
*Assistant Examiner* — David Z Huang
(74) *Attorney, Agent, or Firm* — Westerman, Hattori, Daniels & Adrian, LLP

(57) ABSTRACT

A cleaning chamber is provided in a seal holder and two cleaning chamber flow paths communicating with the cleaning chamber from outside are provided. A pipe connected to a vessel storing a mobile phase is connected to one of the cleaning chamber flow paths. A pipe as a flow path connected to a mobile phase sucking flow path into a pump chamber is connected to the other cleaning chamber flow path. When the mobile phase is taken in, the mobile phase is sucked into the pump chamber via the cleaning chamber.

2 Claims, 2 Drawing Sheets

SOLVENT DELIVERY PUMP AND LIQUID CHROMATOGRAPH

BACKGROUND OF THE INVENTION

1. Field of the Invention

The present invention relates to a solvent delivery pump for sucking and discharging a mobile phase by reciprocating a plunger on a straight line and a liquid chromatograph using the solvent delivery pump.

2. Description of the Related Art

In a solvent delivery pump used for sending a mobile phase in a liquid chromatograph, if the solution sending pressure becomes high over 50 MPa, frictional force between a plunger seal sealing a pump chamber and a plunger becomes large. This shortens the life of the plunger seal. Therefore, in order to reduce the frictional force between the plunger seal and the plunger, a mechanism for supplying a cleaning solution to portions of the plunger seal and the plunger sliding on each other to wet an outer peripheral face of the plunger is proposed (see Japanese Patent Application Laid-Open No. 10-238475).

FIG. 3 shows an example of a solvent delivery pump having such a function. At the tip end of a pump body 2, a pump head 8 having, in itself, a pump chamber 8a, a sucking flow path 8b, and a discharge flow path 8c is provided. A cross head 4 is housed in the pump body 2 and biased in a direction opposite from the pump head 8 by a spring 6. A plunger 3 is retained on the tip end of the cross head 4 and the tip end of the plunger 3 is inserted into the pump chamber 8a.

The cross head 4 is reciprocated on a straight line (in a left-right direction in the drawing) by a driving mechanism (not shown) including a cam and the like, and the plunger 3 also reciprocates on a straight line as the cross head 4 reciprocates to thereby increase and decrease a capacity in the pump chamber 8a. The sucking flow path 8b is connected, via a check valve 10a, to a pipe 29 connected to a vessel for storing the mobile phase. The discharge flow path 8c is connected, via a check valve 10b, for example, to a pipe 28 forming an analytical flow path of the liquid chromatograph.

Between the tip end portion of the pump body 2 and the pump head 8, a plunger seal 12, a seal holder 14, and a cleaning seal 16 are sandwiched in this order from a side of the pump head 8. The plunger seal 12 is for sealing the pump chamber 8a while slidably retaining the plunger 3 at a portion of the pump chamber 8a, into which the plunger 3 is inserted, and the plunger seal 12 is supported on the seal holder 14.

The seal holder 14 includes, in itself, a cleaning chamber 18a and cleaning chamber flow paths 20a and 24a. A pipe 21 assembled to take in a cleaning solution from a vessel storing the cleaning solution with a pump (not shown) to supply it to the cleaning chamber 18a is connected to the cleaning chamber flow path 20a, and a pipe 25 assembled to return the cleaning solution from the cleaning chamber 18a to a vessel for the cleaning solution is connected to the cleaning chamber flow path 24a. The cleaning chamber 18a is sealed with the cleaning seal 16.

By providing a circulating mechanism of the cleaning solution as described above, the cleaning solution is supplied to the cleaning chamber 18a to wet an outer peripheral face of the plunger 3 on a back face side of the plunger seal 12 to reduce friction and increase a sliding property between the plunger 3 and the plunger seal 12. By constantly wetting the back face side of the plunger seal 12, an effect of preventing deposition of salt caused by drying of the back face side of the plunger seal 12 can be obtained.

The above-described solvent delivery pump is provided with vessels for storing the cleaning solution and the pump for circulating the cleaning solution. If these vessels and pump can be omitted, it is possible to reduce the size of a device to reduce an installation space for the device. Moreover, if the pipes for circulating the cleaning solution can be omitted, connection of the pipes is simplified and it becomes easier to detach or assemble the pipes in maintenance. Conventionally, however, it is difficult to reduce the frictional force between the plunger and the plunger seal without such a mechanism.

SUMMARY OF THE INVENTION

It is therefore an object of the present invention to reduce frictional force between a plunger and a plunger seal without separately providing a mechanism for circulating a cleaning solution.

A solvent delivery pump according to the present invention includes: a pump chamber including a sucking port for sucking a mobile phase and a discharge port for discharging the sucked mobile phase; a plunger which has the tip end portion inserted into the pump chamber and which reciprocates on a straight line while sliding in the solvent delivery pump to increase and decrease a capacity in the pump chamber; a plunger seal disposed at a portion of the pump chamber through which the plunger is inserted to retain the plunger and to seal the pump chamber; a mobile phase sucking flow path having one end connected to the sucking port of the pump chamber to suck the mobile phase into the pump chamber; a cleaning chamber which is provided on an opposite side of the plunger seal from the pump chamber to clean an outer peripheral face of the plunger with the mobile phase and through which the mobile phase flows; and a mobile phase flow path connecting the cleaning chamber flow path through which the mobile phase flows from the cleaning chamber and the mobile phase sucking flow path into the pump chamber.

A liquid chromatograph according to the invention includes: a mobile phase sending portion having the solvent delivery pump and sending the mobile phase into an analytical flow path; an analytical column disposed on a downstream side of the mobile phase sending portion with respect to a flow of the mobile phase in the analytical flow path; a sample injecting portion disposed between the mobile phase sending portion and the analytical column in the analytical flow path to inject the sample into the analytical flow path; and a detector disposed on a downstream side of the analytical column in the analytical flow path.

With the solvent delivery pump according to the invention, the cleaning chamber is disposed on the mobile phase sucking flow path having one end connected to the sucking port of the pump chamber to suck the mobile phase into the pump chamber, and therefore the mobile phase which is sucked into the pump chamber necessarily passes through the cleaning chamber. In this way, it is possible to wet an outer peripheral face of the plunger with the mobile phase. Therefore, without separately providing a mechanism for supplying a cleaning solution to the cleaning chamber, it is possible to reduce friction between the plunger seal and the plunger. As a result, an independent mechanism for circulating the cleaning solution becomes unnecessary, installation space for the solvent delivery pump can be reduced, and a piping structure can be simplified.

Because the solvent delivery pump in the invention is used as the solvent delivery pump for sending the mobile phase in the liquid chromatograph in the invention, an installation space for the liquid chromatograph can be reduced and the piping structure can be simplified.

DETAILED DESCRIPTION OF THE INVENTION

Figure 1:
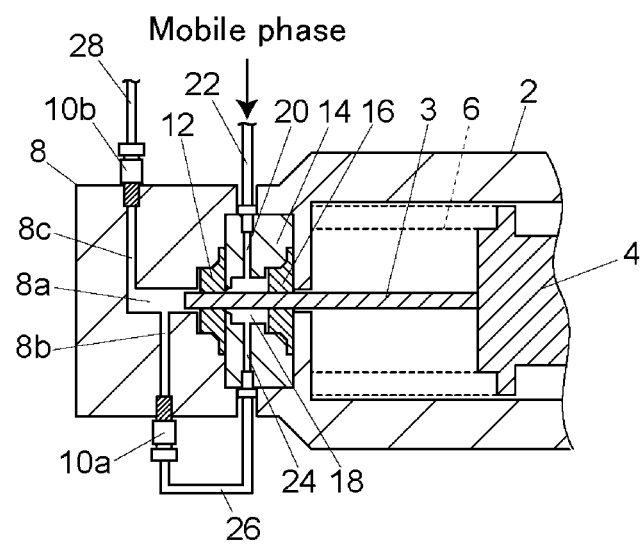
FIG. 1 is a sectional view showing an embodiment of a solvent delivery pump.

An embodiment of a solvent delivery pump will be described with reference to FIG. 1. A pump head 8 is provided to the tip end portion of a pump body 2. The pump head 8 includes, in itself, a pump chamber 8a, a sucking flow path 8b, and a discharge flow path 8c. The sucking flow path 8b is a flow path for taking a mobile phase into the pump chamber 8a and one end of a pipe 26 as a mobile phase flow path is connected to an end portion of the sucking flow path 8b via a check valve 10a. The other end of the pipe 26 is connected to a flow path 24 of a seal holder 14 which will be described later. The discharge flow path 8c is a flow path for discharging the mobile phase sucked into the pump chamber 8a and a pipe 28 is connected to an end portion of the discharge flow path 8c via a check valve 10b. The pipe 28 for example forms an analytical flow path connected from an analytical column of a liquid chromatograph to a detector.

A cross head 4 is housed in the pump body 2 and a plunger 3 extending toward the pump head 8 is retained on the tip end of the cross head 4. The tip end portion of the plunger 3 is inserted into the pump chamber 8a. The cross head 4 is biased in a direction opposite from the pump head 8 by a spring 6. The cross head 4 is reciprocated in the direction toward the pump head 8 and in the opposite direction by a cam mechanism (not shown), and the plunger 3 reciprocates while sliding in the pump chamber 8a as the cross head 4 reciprocates.

The check valves 10a and 10b are opened and closed by utilizing, for example, a difference in pressure to prevent back-flow of the mobile phase. In other words, if the plunger 3 moves in the direction opposite from the pump head 8, pressure in the pump chamber 8a is reduced, the check valve 10a is opened, the check valve 10b is closed, and the mobile phase is sucked into the pump chamber 8a. On the other hand, if the plunger 3 moves toward the pump head 8, the inside of the pump chamber 8a is pressurized, the check valve 10a is closed, the check valve 10b is opened, and the mobile phase in the pump chamber 8a is discharged.

A portion of the pump chamber 8a into which the plunger 3 is inserted is sealed with a plunger seal 12. The plunger seal 12 is supported on a flange 14 sandwiched between the pump body 2 and the pump head 8. The plunger seal 12 has a hole through which the plunger 3 passes and prevents leakage of the mobile phase from the pump chamber 8a while slidably retaining the plunger 3.

The seal holder 14 includes, in itself, a cleaning chamber 18. In the seal holder 14, two cleaning chamber flow paths 20 and 24 made up of through holes communicating with the cleaning chamber 18 from outside are provided. The cleaning chamber 18 is sealed, on a side of the pump body 2, with a cleaning seal 16. The cleaning seal 16 is supported on the tip end face of the pump body 2. A pipe 22 connected to a vessel storing the mobile phase is connected to the cleaning chamber flow path 20. As described above, the other end of the pipe 26 is connected to the cleaning chamber flow path 24. The pipe 22, the cleaning chamber flow paths 20 and 24, the pipe 26, and the sucking flow path 8b form a flow path through which the mobile phase flows.

In the solvent delivery pump in the embodiment, the sucking flow path 8b is connected to the one cleaning chamber flow path 24 connected to the cleaning chamber 18 via the pipe 26 and the pipe 22 connected to the vessel storing the mobile phase is connected to the other cleaning chamber flow path 20 connected to the cleaning chamber 18. Therefore, the mobile phase which is sucked into the pump chamber 8a necessarily passes through the cleaning chamber 18. In this way, it is possible to wet an outer peripheral face of the plunger 3 with the mobile phase on a back face side (on the opposite side from the pump chamber 8a) of the plunger seal 12. Therefore, without requiring independent pump and piping for supplying a cleaning solution which is different from the mobile phase to the cleaning chamber 18, it is possible to reduce friction between the outer peripheral face of the plunger 3 and the plunger seal 12 to prevent shortening of life of the plunger seal 12.

Figure 3:
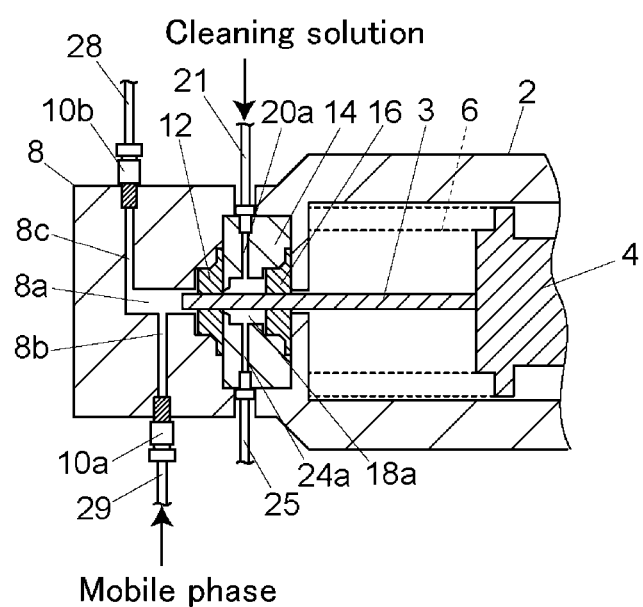
FIG. 3 is a sectional view showing an embodiment of a conventional solvent delivery pump.

If the mobile phase is a buffer solution including salt, the buffer solution which has passed through the cleaning chamber 18 adheres to the outer peripheral face of the plunger 3, the buffer solution which leaks to the back face side of the cleaning seal 16 dries, and the salt is deposited and enters between the plunger 3 and the cleaning seal 16, which may shorten the life of the cleaning seal 16. Therefore, if the mobile phase is the buffer solution including the salt, an analyst reassembles the pipes to form the conventional flow path for causing the cleaning solution which is different from the mobile phase to flow through the cleaning chamber 18 as shown in FIG. 3.

Figure 2:
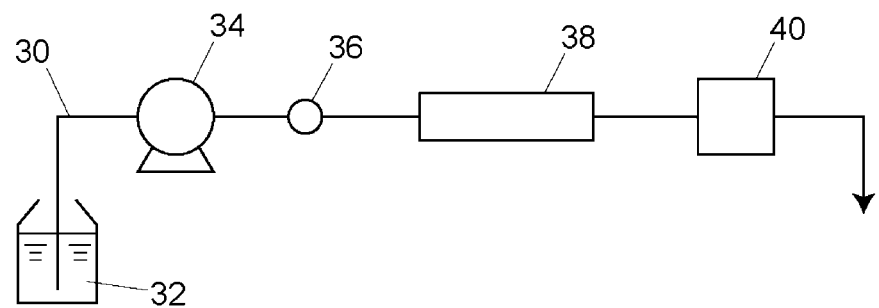
FIG. 2 is a sectional view showing an embodiment of a liquid chromatograph.

Next, the liquid chromatograph using the solvent delivery pump in the above embodiment will be described by using FIG. 2. A solvent delivery pump 34, a sample injecting portion 36, an analytical column 38, and a detector 40 are provided in this order from an upstream side of a flow of the mobile phase in an analytical flow path 30. An upstream end of the analytical flow path 30 is connected to a vessel 32 storing the mobile phase. As the solvent delivery pump 34, the solvent delivery pump in the embodiment in FIG. 1 is used.

The mobile phase sent by driving the plunger 3 of the solvent delivery pump 34 wets the outer peripheral face of the plunger 3 in the cleaning chamber 18 and is sucked into the pump chamber 8a and discharged. The mobile phase discharged from the pump chamber 8a of the solvent delivery pump 34 carries a sample injected from the sample injecting portion 36 to the analytical column 38. In the analytical column 38, the sample is separated into respective ingredients which are respectively detected by the detector 40.

The invention claimed is:
1. A solvent delivery pump comprising:
a pump chamber including a sucking port for sucking a mobile phase and a discharge port for discharging the sucked mobile phase;
a plunger having a tip end portion inserted into the pump chamber and reciprocating on a straight line while sliding in the solvent delivery pump for increasing and decreasing a capacity in the pump chamber;
a plunger seal disposed at a portion of the pump chamber through which the plunger is inserted, the plunger seal retaining the plunger and sealing the pump chamber;
a mobile phase sucking flow path having one end connected to the sucking port of the pump chamber for sucking the mobile phase into the pump chamber;
a cleaning chamber provided on an opposite side of the plunger seal from the pump chamber for cleaning an outer peripheral face of the plunger with the mobile phase, through which the mobile phase flows; and a mobile phase flow path connecting a cleaning chamber flow path wherein the mobile phase flows through the cleaning chamber to the mobile phase sucking flow path.

2. A liquid chromatograph comprising:

a mobile phase sending portion having the solvent delivery pump according to claim 1 and sending the mobile phase into an analytical flow path;

an analytical column disposed on a downstream side of the mobile phase sending portion with respect to a flow of the mobile phase in the analytical flow path;

a sample injecting portion disposed between the mobile phase sending portion and the analytical column in the analytical flow path for injecting a sample into the analytical flow path; and a detector disposed on a downstream side of the analytical column in the analytical flow path.

* * * * *